(12) United States Patent
Causevic et al.

(10) Patent No.: US 8,391,948 B2
(45) Date of Patent: Mar. 5, 2013

(54) ELECTRODE ARRAY

(75) Inventors: Elvir Causevic, Clayton, MO (US);
Christian Christiansen, Birkeroed (DK); Daniel Metzger, Belleville, IL (US)

(73) Assignee: Brainscope Company, Inc., Bethesda, MD (US)

( * ) Notice: Subject to any disclaimer, the term of this patent is extended or adjusted under 35 U.S.C. 154(b) by 946 days.

(21) Appl. No.: 12/067,525

(22) PCT Filed: Sep. 22, 2006

(86) PCT No.: PCT/US2006/037045
§ 371 (c)(1),
(2), (4) Date: Aug. 18, 2008

(87) PCT Pub. No.: WO2007/038305
PCT Pub. Date: Apr. 5, 2007

(65) Prior Publication Data
US 2009/0018427 A1  Jan. 15, 2009

Related U.S. Application Data

(60) Provisional application No. 60/719,943, filed on Sep. 23, 2005.

(51) Int. Cl.
*A61B 5/0478* (2006.01)
*A61B 5/0484* (2006.01)

(52) U.S. Cl. ......... 600/383; 600/393; 600/544; 600/559

(58) Field of Classification Search ................... 600/383, 600/393, 544, 546, 547, 559
See application file for complete search history.

(56) References Cited

U.S. PATENT DOCUMENTS
3,762,396 A  10/1973  Ballentine et al.
(Continued)

FOREIGN PATENT DOCUMENTS
JP  05-261076  12/1993

OTHER PUBLICATIONS
International Search Report and Written Opinion for PCT/US2006/037045, mailed Mar. 20, 2007 from the International Searching Authority of the United States Patent and Trademark Office.
(Continued)

*Primary Examiner* — Lee S Cohen
(74) *Attorney, Agent, or Firm* — Finnegan, Henderson, Farabow, Garrett & Dunner LLP

(57) ABSTRACT

A disposable electrode array 100, 200 including a flexible member 106, 206 in which a plurality of electrodes 102, 202 are disposed, having a shape adapted to contact the forehead skin surface on a human patient. A pair of ear loops 104, 204 coupled to the disposable electrode array 100, 200 secure the disposable electrode array 100, 200 about the patient's ears, with the flexible member 106, 206 disposed across the patient's bow, retaining the electrodes 102, 202 against the skin surface. Additional electrodes 102, 202 are disposed in proximity to the ear loops 104, 204 and are configured to contact the skin surface behind the patient's ears. An auditory stimulus delivery element 116, 216 is coupled with each of the ear loops 104, 204, and positioned to seat in proximity to the patient's ear canal for the delivery of auditory stimulus. Electrical conductors associated with the electrodes 102, 202 and the stimulus delivery elements 116, 216 are routed within the flexible member 106, 206 to a common external connection point 118, 218 for connection to an external system. The disposable electrode array 100, 200 may be configured for both evoking and measuring evoked bio-potentials in the human subject, or for measuring bio-potentials evoked using a separate stimulus delivery system.

17 Claims, 2 Drawing Sheets

U.S. PATENT DOCUMENTS

| | | | | |
|---|---|---|---|---|
| 4,359,724 A | * | 11/1982 | Zimmerman et al. | 600/383 |
| 4,595,013 A | | 6/1986 | Jones et al. | |
| 4,928,696 A | * | 5/1990 | Henderson et al. | 600/383 |
| 5,479,934 A | * | 1/1996 | Imran | 600/544 |
| 5,800,351 A | | 9/1998 | Mann | |
| 6,077,237 A | * | 6/2000 | Campbell et al. | 600/587 |
| D560,809 S | * | 1/2008 | Causevic et al. | D24/187 |
| 2005/0059899 A1 | * | 3/2005 | Merilainen et al. | 600/544 |
| 2007/0106169 A1 | * | 5/2007 | Fadem | 600/383 |

OTHER PUBLICATIONS

Office Action dated Nov. 29, 2011, issued by the Japanese Patent Office for corresponding Japanese Application No. 2008-532427, including cited Japanese Utility Model Application No. 7-28503.

* cited by examiner

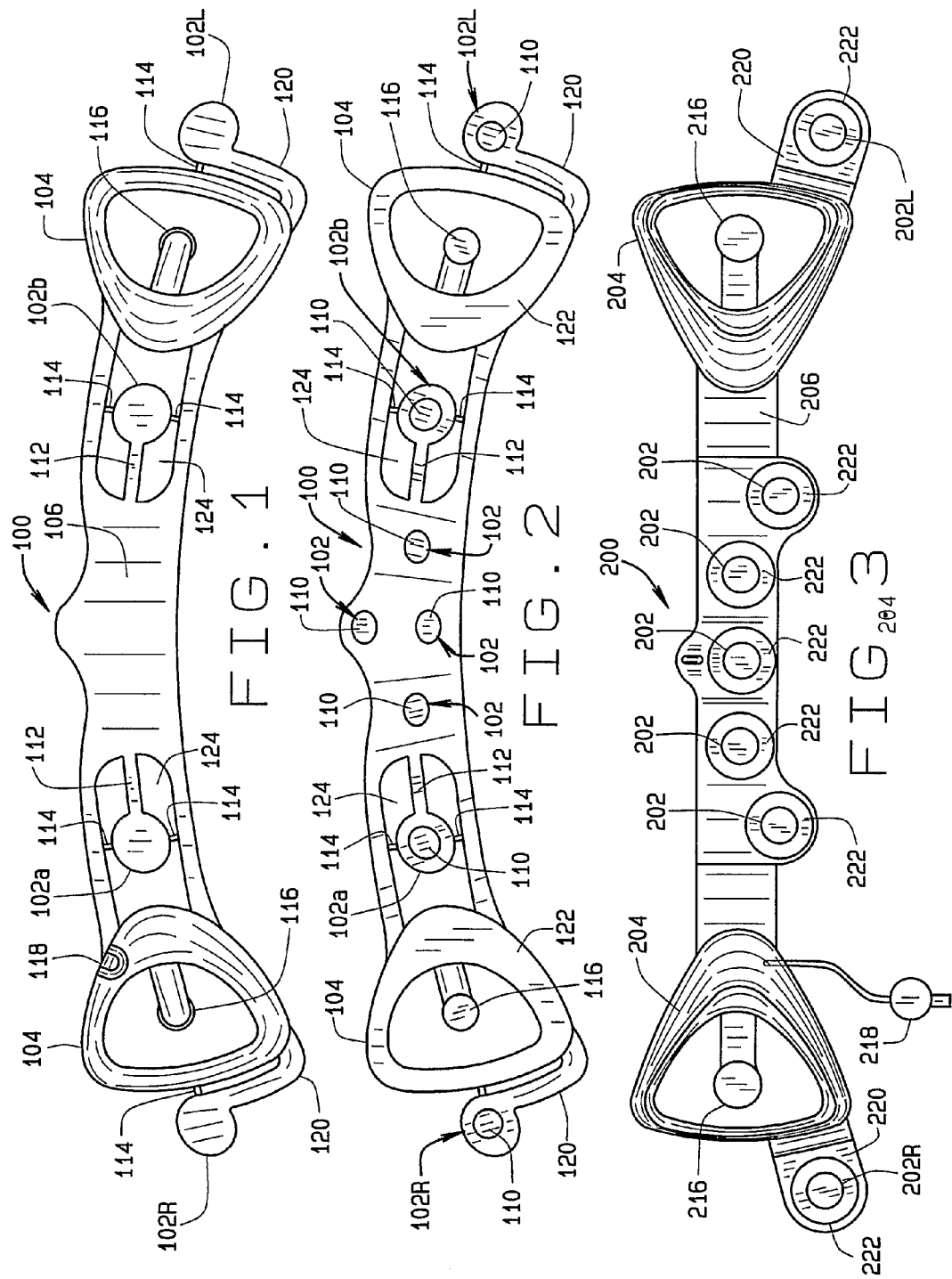

ELECTRODE ARRAY

CROSS-REFERENCE TO RELATED APPLICATIONS

The present application is related to, and claims priority from, U.S. Provisional Patent Application Ser. No. 60/719,943 filed on Sep. 23, 2005, which is herein incorporated by reference.

TECHNICAL FIELD

The present invention related generally to electrodes for receiving bio-potential signals from skin surfaces of a human patient, and in particular, to a disposable electrode array integrating auditory evoked potential (AEP) and electro-encephalogram (EEG) electrodes into a single appliance for adjustable placement on the head of a human patient.

BACKGROUND ART

When multiple nerve cells or muscle cells depolarize simultaneously or sequentially, they generate a bio-potential that can be detected as an electrical signal by an externally positioned electrical circuit. External electrical circuits have long been used to measure such relatively small but measurable bio-potentials. The electroencephalogram (EEG) and Auditory Evoked Potential (AEP) are examples of signals used to monitor brain cell activity.

Electrode apparatus for recording bio-potentials, for example for EEG biofeedback applications, include a minimum of one pair of electrodes, and a third electrode as the ground electrode. The pair of electrodes, including an "active" electrode and an "indifferent" electrode, record one channel of EEG signal. The active electrode is typically located on the head near a brain area being monitored, the indifferent electrode is located on the head, on an ear, or on the mastoid bone behind an ear, and the ground electrode is typically placed on the forehead or on an ear, but can be placed almost anywhere. Additional recording channels can be added as desired by adding additional electrodes.

Known electrodes and related apparatus for recording bio-potentials such as EEG's are disposable electrodes such as, but not limited to, disposable self-adhesive individual electrodes, ear clip electrodes, disc electrodes, needle electrodes and saline-based electrodes. With all types of electrodes, a key factor in obtaining accurate and relatively noiseless bio-potential recordings is maintaining adequate contact between the electrode and the skin, because bio-potentials are typically relatively small, i.e. less than about 20 mV, and the recordings are highly susceptible to noise and artifacts.

While the methods of ensuring proper electrical contact between the electrode and the skin vary somewhat with the type of electrode being used, the skin usually must be prepared by cleaning with alcohol and abrading with an electrode preparation gel. The steps of cleaning and abrading may be repeated several times for ideal surface preparation. Skin contact is established using an ear clip electrode with a metal clip that fastens to the outer ear, a self-adhesive disc electrode that adheres directly to an area of skin, or with a disc electrode having a cup that is filled with an electrode paste. These types of electrodes are unsuitable for use in areas with much hair, such as on the scalp, and generally provide electrical contact that is not very robust or long lasting, which affects the quality and duration of recordings that can be obtained.

Needle-type electrodes generally provide better and more long-lasting contact, and can be used on the scalp, but involves tedious, uncomfortable and costly procedure to secure contact. To utilize a needle-type electrode, the hair must be parted to reveal skin, a colloidin-treated gauze layer secured over the electrode, electrode gel injected with a hypodermic needle through a hole in an electrode cup, and finally the skin abraded with the blunt end of the needle.

Headband-type and hat-style electrode connectors which completely encircle the head of a patient are known, in which electrodes such as those described above, are coupled to a hat, or to a headband made of an elastomeric material that fits around the crown of the head, holding cup or disc-type electrodes in place across the forehead of the subject. Headband-type electrode connectors are typically used for recording signals from the frontal areas of the brain, and are less useful for recording from other areas of the brain because of the relatively poor signal quality that results. In addition, headband connectors still require careful skin preparation.

Saline-based electrodes are also known, in which salt water is used to maintain the electrical connection between electrode and skin, instead of electrode gel. An electrode connector such as a headband or clip is required for securing the electrodes to the head, and skin preparation is still required. Further, to maintain the proper electrical contact, the electrode placements must be carefully monitored to ensure that the mechanical contact is maximized and that the electrodes stay sufficiently wetted with the saline-based solution.

Each of the above-described electrodes and electrode apparatus may be utilized to monitor and record bio-potentials. The bio-potentials may be continuous, representative of normal brain activity, or may be evoked in response to an external stimuli. External stimuli may be provided to any of the sensory systems of a human body, and may include auditory stimuli delivered to the ear of the patient by a suitable delivery mechanism. Conventionally, the delivery mechanism for the external stimuli is separate from the electrodes employed to measure the evoked response, requiring additional setup and handling.

Known electrode apparatus and connectors are therefore limited by being annoying or uncomfortable for the subject, especially when placed on the head. With the additionally requirement of setting up a stimuli delivery system, the task can quickly become unduly complicated and time consuming. The discomfort or apprehension associated with the setup is a particular problem for children, infants, and uncooperative subjects. Interference by an uncooperative subject with the placement and contact of head electrodes can render recordings of evoked brain potentials impossible to obtain or useless because of minimal or inadequate contact.

A need therefore exists for an electrode apparatus configured adapted to deliver stimuli for measuring evoked potentials which is simply and comfortably positioned on the subject, which maintains adequate skin contact for obtaining measurable recordings, and which is readily and inexpensively adapted for use with small children and infants.

SUMMARY OF THE INVENTION

An apparatus of the present invention is provided for evoking and measuring bio-potentials in a human subject. In a preferred embodiment, the apparatus includes a flexible member in which a plurality of electrodes are disposed, having a shape adapted to contact the forehead skin surface on a human subject. A pair of ear loops coupled to the apparatus secure the apparatus about the patient's ears, retaining the electrodes against the skin surface. Additional electrodes are disposed in proximity to the ear loops and are configured to contact the skin surface behind the patient's ears. An auditory stimulus delivery element is coupled to the ear loops, and positioned to seat in proximity to the patient's ear canal for the delivery of auditory stimulus. The apparatus is used for both evoking and measuring evoked bio-potentials in the human subject, or for measuring bio-potentials evoked using a separate stimulus delivery system.

The foregoing features, and advantages of the invention as well as presently preferred embodiments thereof will become more apparent from the reading of the following description in connection with the accompanying drawings.

BRIEF DESCRIPTION OF THE DRAWINGS

In the accompanying drawings which form part of the specification:

FIG. 1 is a top plan view of an electrode array of the present invention;

FIG. 2 is a bottom plan view of the electrode array of FIG. 1;

FIG. 3 is a top plan view of an alternate embodiment electrode array of the present invention;

Corresponding reference numerals indicate corresponding parts throughout the several figures of the drawings. It is to be understood that the drawings are for illustrating the concepts of the invention and are not to scale.

BEST MODES FOR CARRYING OUT THE INVENTION

The following detailed description illustrates the invention by way of example and not by way of limitation. The description enables one skilled in the art to make and use the invention, and describes several embodiments, adaptations, variations, alternatives, and uses of the invention, including what is presently believed to be the best mode of carrying out the invention.

The present invention provides a disposable electrode array 100 adapted to quickly and properly apply required electrode sensors to a patient. The disposable electrode array 100 integrates a set of electrode sensors 102, such as AEP sensors and EEG sensors, into a one-piece array. The electrode sensors 102 are adjustable to permit the placement of the electrode sensors 102 to the individual patient. Preferably, the use of elastic materials in the construction of the disposable electrode array 100 enables the electrode appliance to accommodate a variety of patient head sizes and shapes. Ear loops 104 disposed at opposite ends of a central band 106 the disposable electrode array 100 are adapted for placement around the ears of the individual patient to anchor the disposable electrode array 100 to the patient's head during use, and to eliminate movement of the disposable electrode array 100 during testing procedures.

Figure 4:
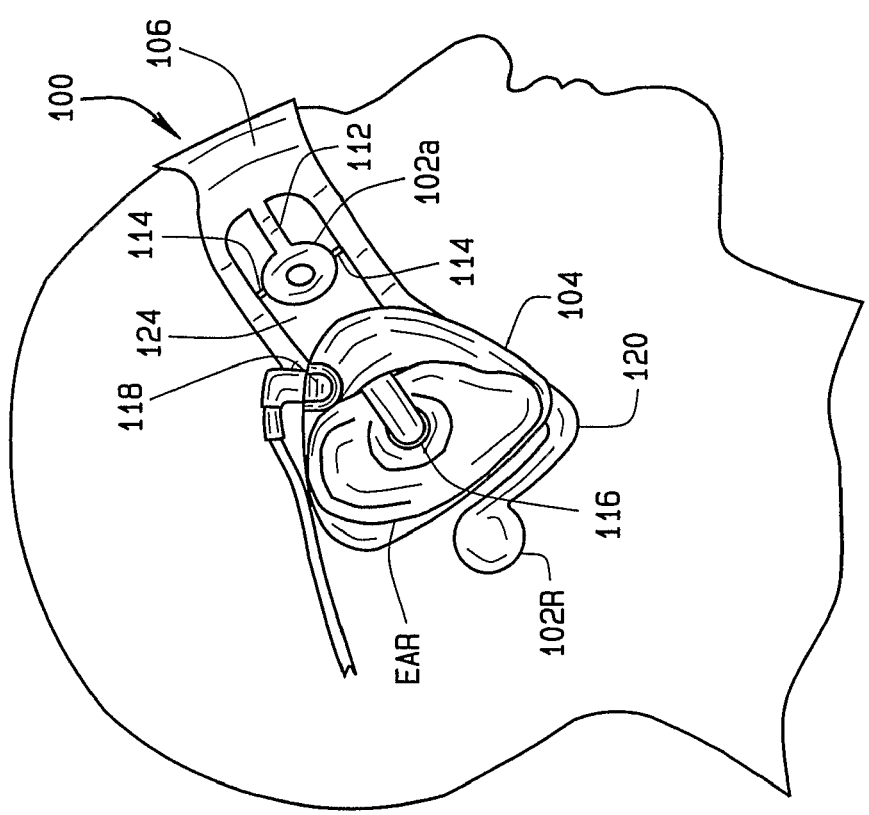
FIG. 4 is a perspective side view of the electrode array of FIG. 1 secured to a patient's head.

As seen in FIGS. 1 and 2, in a first embodiment of the present invention, the central band 106 is composed of a flexible web of material disposed between the pair of ear loops 104, and supports a plurality of individual electrodes 102. Each electrode has an exposed electrically conductive surface or receptor region 110 adjacent a common side of the disposable electrode array 100 for placement against the skin of a patient when in use. When the ear loops 104 are secured about the ears of a human patient, as shown in FIG. 4, the common side of the flexible web 106 is retained, preferably in tension, against the brow of the human patient, and the electrodes 102 disposed within the flexible web 106 are operatively held in place against the skin surface of the human patient.

As best seen in FIGS. 1 and 2, some of the electrodes 102 within the flexible web 104, such as electrodes 102a and 102b, are coupled to the flexible web by one or more flexible connectors 112 and secured temporarily in place by associated break-away tabs 114. During placement of the disposable electrode array 100 on a patient, some or all of the break-away tabs 114 may be intentionally severed, allowing the associated electrodes 102 to be repositioned against the patient's skin surface within an area limited by the range of motion of the associated flexible connectors 112, thereby facilitating ideal placement of the electrodes 102 on the skin of the human patient.

An auditory stimulator 116, such as a speaker or other suitable device, may be disposed within each ear loop 104, and is adapted for placement in proximity to an ear canal of the human patient when the ear loop 104 is disposed about the human patient's ear. Auditory signals may delivered to the ear canal via the auditory stimulator 116 during auditory testing or the triggering of auditory evoked potential signals.

Figure 5:
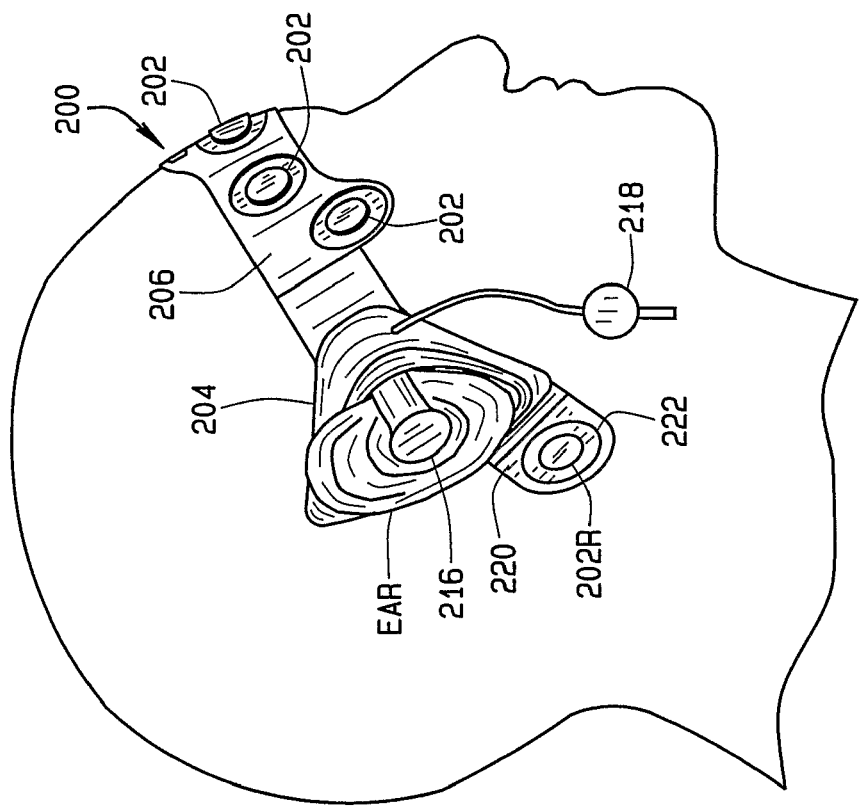
FIG. 5 is a perspective side view of the electrode array of FIG. 3 secured to a patient's head.

For convenience, electrically conductive leads to each electrode 102, and to the auditory simulators 116, may be routed internally within the structure of the disposable electrode array 100 to a common connection point 118, at which an external connector or lead (not shown) linking the electrodes 102 and auditory simulators 116 to an external power and/or control device (not shown) may be removably coupled. As is seen in FIGS. 4 and 5, it is preferable that the common connection point 118 be disposed on one of the ear loops 104, allowing the external connector or lead to be routed over the patient's ear or away from the patient's face during use.

In addition to the electrodes 102 disposed within the flexible web 106 between the pair of ear loops 104, ear loop electrodes 102L and 102R may be disposed on associated flexible extension 120 coupled to the ear loops 104, opposite from the central portion of the flexible web 106, as best seen in FIGS. 1-2. Electrodes 102L and 102R disposed on the associated flexible extensions 120 are configured for placement in proximity to a human patient's mastoid bones when the ear loops 104 are placed about the patient's ears.

To provide a comfortable fit to the human patient, the ear loops 104 and flexible web 106 are preferably constructed with a laminated foam layer. The ear loops 104 may be either rigid or flexible to accommodate different ear sizes. Optionally, a layer of adhesive foam 122 may be placed around each of the ear loops 104 and/or electrodes 102 to facilitate maintaining the electrodes 102 in place against the patient's skin surface during use, and to prevent any electrolytic gel associated with the electrodes 102 from being displaced and potentially providing an electrical conduit between adjacent electrodes 102.

Those of ordinary skill will recognize that the disposable electrode array 100 may be manufactured in a variety of different sizes suitable for use with patients of different ages. For example, a smaller electrode array with flexible ear loops may be suitable for use with an infant or young child, while a larger electrode array with rigid ear loops may be suitable for use with an adult patient.

Those of ordinary skill in the art will further recognize that the specific number and configuration of the electrodes 102 within the disposable electrode array 100 may be varied depending upon the particular application for which the electrode array 100 is intended to be used. For example, as seen in FIGS. 1 and 2, a portion of the electrodes 102 may be disposed in a fixed configuration near the center portion of the flexible web 106 for placement against the brow of a patient when in use. An electrode 102a and 102b, supported on the flexible connector 112 by one or more break-away tabs 114 may be disposed within openings 124 in the flexible web 106 between the set of fixed electrodes 102 and each ear loop 104. If the placement of these supported electrodes 102a and 102b is not ideal when the electrode array 100 is positioned against a patient's head, the break-away tabs 114 may be severed, and the electrodes 102a and 102b may be repositioned within the opening 124 in the flexible web 106 as needed to achieve an ideal placement. Similarly, the electrodes 102L and 102R associated with each ear loop 104 may be adjustably disposed opposite from the central portion of the flexible web 106, for placement against a patient's mastoid bone.

In an alternate embodiment of the disposable electrode array, shown at 200 in FIGS. 3 and 5, a set of electrodes 202 is disposed in a generally fixed configuration on a central band 206. The central band 206 is composed of a flexible web disposed between the pair of ear loops 204, and supports a plurality of individual electrodes 202. Each electrode 202 has an exposed electrically conductive surface or receptor region adjacent a common side of the disposable electrode array 200 for placement against the skin of a patient when in use. When the ear loops 204 are secured about the ears of a human patient, as shown in FIG. 5, the common side of the flexible web 206 is retained in tension against the brow of the human patient, and the electrodes 202 disposed within the flexible web 206 are operatively held in place against the skin surface of the human patient.

An auditory stimulator 216, such as a speaker, may be disposed within each ear loop 204, and is adapted for placement in proximity to an ear canal of the human patient when the ear loop 204 is disposed about the human patient's ear. Auditory signals may delivered to the ear canal via the auditory stimulator 216 during auditory testing or the triggering of auditory evoked potential signals.

For convenience, electrically conductive leads to each electrode 202 and to the auditory simulators 216 may be routed internally within the disposable electrode array 200 to a common connection point 218 at which an external connector or lead (not shown) linking the electrodes 202 and auditory simulators 216 to an external power and/or control device (not shown) may be removably coupled. As is seen in FIG. 5, it is preferable that the common connection point 218 be disposed on one of the ear loops 204, allowing the external connector or lead to be routed over the patient's ear or away from the patient's face.

In addition to the electrodes 202 disposed within the flexible web 206 between the pair of ear loops 204, some electrodes 202L and 202R may be disposed on flexible extension 220 coupled to the ear loops 204, opposite from the central portion of the flexible web 206, as best seen in FIG. 3. Electrodes 202L and 202R disposed on the extensions 220 are configured for placement in proximity to a human patient's mastoid bones when the ear loops 204 are placed about the patient's ears. Optionally, the electrodes 202R and 202L associated with the ear loops 204 may be eliminated, and all of the electrodes 202 in the electrode array 200 may be disposed in a fixed configuration between the ear loops on the flexible web 206.

To provide a comfortable fit to the human patient, the ear loops 204 and flexible web 206 are preferably constructed with a laminated foam layer. The ear loops 204 may be either rigid or flexible to accommodate different ear sizes. Optionally, a layer of adhesive foam 222 may be placed around each of the ear loops 204 and/or electrodes 202 to facilitate maintaining the electrodes 202 in place against the patient's skin surface during use, and to prevent any electrolytic gel associated with the electrodes 202 from being displaced and potentially providing an electrical conduit between adjacent electrodes 202.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

The invention claimed is:

1. An electrode array for measuring bio-potential signals from a skin surface, consisting essentially of:
   a pair of ear loops, each ear loop configured to fit around an ear of a human patient, and each ear loop further comprising at least one ear loop electrode;
   a flexible web coupled between said pair of ear loops and supporting a plurality of electrodes thereon, said flexible web configured to span a forehead of said human patient, and said plurality of electrodes configured for placement against a skin surface on the forehead of said human patient;
   wherein the ear loops and the flexible web are configured to retain the flexible web in tension across the forehead of said human patient and to position the plurality of electrodes operatively in place on the forehead when the pair of ear loops are secured about the ears of the human patient.

2. The electrode array of claim 1 wherein each of said plurality of electrodes is operatively coupled via an associated electrical conductor to a common external connection point.

3. The electrode array of claim 2 wherein each of said associated electrical conductors is routed internally through said flexible web.

4. The electrode array of claim 1 further including an auditory stimulator centrally disposed within each of said pair of ear loops for placement adjacent an ear canal, each of said auditory stimulators configured to generate an auditory stimuli.

5. The electrode array of claim 4 wherein each of said auditory stimulators is operatively coupled via an associated electrical conductor to a common external connection point.

6. The electrode array of claim 1 wherein said at least one ear loop electrode is disposed about said ear loop substantially opposite from said flexible web.

7. The electrode array of claim 1 further including an adhesive material disposed around each of said electrodes.

8. The electrode array of claim 1 further including an external connection for establishing an electrical connection to each of said plurality of electrodes.

9. The electrode array of claim 1 wherein each of said ear loops is composed of a flexible material.

10. The electrode array of claim 1 wherein each of said ear loops is composed of a substantially rigid material.

11. The electrode array of claim 1 wherein at least one electrode in said plurality of electrodes is secured to said flexible web with at least one break-away tab and supported on at least one flexible connector coupled to said flexible web, said at least one flexible connector configured to permit a range of movement of said electrode following severing of said at least one break-away tab to facilitate placement of said electrode on said skin surface.

12. The electrode array of claim 11 wherein at least four electrodes are disposed within a central portion of said flexible web in a fixed configuration.

13. The electrode array of claim 1 wherein each of said at least one ear loop electrodes is supported on an associated flexible connector coupled to said ear loop, and is secured to said ear loop with at least one break-away tab, said flexible connector configured to permit a range of movement of said at least one ear loop electrode following severing of said at least one break-away tab to facilitate placement of said at least one ear loop electrode on said skin surface.

14. A method for using an electrode array having a pair of ear loops and a flexible web coupled between said pair of ear loops, each ear loop configured to fit around an ear of a human patient and mounting at least one ear loop electrode, and the flexible web spanning a forehead of the human patient and supporting a plurality of electrodes thereon for placement against a skin surface on the forehead of the human patient, the method including the steps of:
  securing a first ear loop in the pair of ear loops about an ear of the human patient, wherein said step of securing said first ear loop includes positioning the at least one ear loop electrode associated with the first ear loop;
  disposing the flexible web across the forehead of the human patient; and
  securing a second ear loop in the pair of ear loops about an opposite ear of the human patient, wherein said step of securing said second ear loop includes positioning the at least one ear loop electrode associated with the second ear loop;
  whereby the flexible member web is anchored across the forehead of the human patient and is retained in tension against the brow by tension between the pair of ear loops; and whereby
  the plurality of electrodes on the flexible web are operatively positioned on the forehead of the human patient.

15. The method of claim 14 further including the step of altering a position of at least one of said plurality of electrodes independent of the position of said flexible web against said forehead.

16. The method of claim 15 wherein said step of altering said position includes severing at least one break-away connector between at least one of said plurality of electrodes and said flexible web.

17. The method of claim 14 wherein said step of positioning said first ear loop includes positioning the at least one ear loop electrode associated with the first ear loop against the patient's skin in proximity to a mastoid bone; and wherein said step of positioning said second ear loop includes positioning the at least one ear loop electrode associated with the second ear loop against the patient's skin in proximity to the mastoid bone opposite from the at least one ear loop electrode associated with the first ear loop.

* * * * *